(12) United States Patent
Yoshida

(10) Patent No.: US 6,750,372 B1
(45) Date of Patent: Jun. 15, 2004

(54) PROCESS FOR PRODUCING ARYL ETHER

(75) Inventor: Masaaki Yoshida, Tochigi-ken (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/182,399

(22) PCT Filed: Sep. 6, 2000

(86) PCT No.: PCT/JP00/06064

§ 371 (c)(1),
(2), (4) Date: Jul. 30, 2002

(87) PCT Pub. No.: WO01/58836

PCT Pub. Date: Aug. 16, 2001

(30) Foreign Application Priority Data

Feb. 9, 2000 (JP) ........................................ 2000-031761

(51) Int. Cl.$^7$ ............................................... C07C 41/09
(52) U.S. Cl. ...................................... 568/630; 568/631
(58) Field of Search ................................. 568/630, 631

(56) References Cited

FOREIGN PATENT DOCUMENTS

JP 11158114 * 6/1999 ........... C07C/69/28

OTHER PUBLICATIONS

Miyamoto et al., computer generated English translation of JP–11158114.*
Richard J. Lewis, Sr., Hawley's Condensed Chemical Dictionary, twelfth edition, 1993, p. 635).*

* cited by examiner

*Primary Examiner*—Rosalynd Keys
(74) *Attorney, Agent, or Firm*—Sherman & Shalloway

(57) ABSTRACT

A method for producing an aryl ether produced by bonding an aryloxy of hydroxyaryl with an organic group of organic halogen, which comprises reacting hydroxyaryl with organic halogen in gaseous carbon dioxide or supercritical carbon dioxide in the presence of base and catalytic amount of onium salt.

8 Claims, 1 Drawing Sheet

PROCESS FOR PRODUCING ARYL ETHER

FIELD OF THE INVENTION

The present invention relates to a novel producing method for aryl ether compound, more in detail relates to an environmentally harmonized producing method for aryl ether in gaseous or supercritical state of carbon dioxide.

BACKGROUND OF THE INVENTION

In the field of conventional chemistry, the ordinary purpose of it is to provide useful substances to the market. During the progress to achieve above purpose, the effort to reduce the generation of by-products is carried out. However, since the correct evaluation for said by-products from the biological view point was not sufficiently made in those days, many by-products which are negative to the environment from the biological view point were discharged in natural environment.

Among above mentioned circumstance, from the careful observant eyes of the peoples who have ardent interests to the nature, the charge of a mode of life of living things becomes to be realized and many substances causing said changes are also becoming to be realized. That is, the fundamental change to the concept of chemical products is started to be arisen.

Namely, in the development of the technique to make harmless or to remove above-mentioned negative chemical substances, or in the process to produce useful well-known substances, the developments are becoming to be proceeded so as to produce the products which are gentle to the nature or the products which are biologically mimetic materials.

Concerning above-mentioned circumstance, in the field of synthetic chemistry, an effort has been made to design a synthetic process in which products to be wasted or by-products are not generated. Further, even if a case that a by-product is generated, the effort to minimize the influence of the by-product to living things has been carefully made. And, also for the substance to be used in a synthetic process, it is required to use the substance which does not easily cause a chemical accident. According to the above-mentioned understanding, the synthetic reaction using carbon dioxide which is harmless and inflammable, especially using supercritical carbon dioxide which has intermediate function between gas and liquid, as a reactive medium is recognized as a reaction which meets to above mentioned social requirement, and new reaction methods are going to be developed.

Concerning above-mentioned present conditions, in the synthesis of urethane, the inventor of this invention has already proposed the method for reaction of amine and alkyl halide in supercritical carbon dioxide under the presence of a base and onium salt [Chem. Commun., page 151 (2000)], which is similar to the synthetic condition of aryl ether of the present invention.

In the etherification reaction of phenols, the following method was disclosed in Japanese Patent Laid Open Publication 11-236344 published on Aug. 31, 1999). That is, an aromatic compound possessing at least one hydroxyl group on an aromatic ring and can possess a carboxyl group and/or hydrocarbiloxycarbonyl group and a lower alcohol are used as the starting materials, and the method to produce hydrocarbil ether of the aromatic compound by substituting a hydrogen atom of a hydroxyl group on the aromatic ring of said aromatic compound with a hydrocarbil group of lower alcohol is described. In said producing method, a method to react these compounds in the condition in which at least one of carboxylic acids becomes supercritical state in the presence of said aromatic compound, lower alcohol or carboxylic acid In said method, carbon dioxide is used as an inert medium together with argon and methane, however, the reaction temperature higher than the critical temperature of lower alcohol is needed and the yield of the reaction product does not exceed 50%. Further, since the starting materials are quite different from that of the present invention and acidic condition is required for the progress of reaction, said method does not teach the producing method of aryl ether of the present invention. Furthermore, said method does not teach an improved synthetic technology of the conventional producing method of aryl ether in organic solvent using hydroxydiarylethers and organic halogen as the starting materials.

In the meanwhile, aryl ether is a chemical compound used as the synthesis materials of various fields such as liquid crystal, medicines, agricultural chemicals, dyes, synthetic polymer or others. And at the producing process of it, it is popular to use phenols and halogenated alkyl or harmful alkyl sulfate, and harmful and inflammable organic solvent. The wasted organic solvent after used, have a problem to cause an environmental problem when it is discharged.

Therefore, the object of the present invention is to provide a novel improved synthetic technique for producing aryl ether using hydroxyaryls and organic halogen as the starting materials. In the earnest investigation to accomplish said object, the inventor of the present invention has thought of the use of gaseous carbon dioxide or supercritical carbon dioxide which are the environmentally harmonized type fluid as a medium for reaction instead of the use of above mentioned organic liquid state medium. And the inventor of the present invention has investigated to design a system of reaction which allows the synthesis of the aimed compound using above mentioned starting materials in above mentioned medium. In the process of the investigation, the inventor of the present invention has concerned to apply the reactive condition which is proposed by the inventor of the present invention in above mentioned document. That is, said condition is used in the reaction using organic halogenated compound as one starting material and characterizes to make exist a base and onium salt by catalytic amount in the reaction system. By the substantial experiments, the inventor of the present invention have found that there is a reactive condition to produce aryl ether in above mentioned reactive condition, and accomplished the present invention.

DISCLOSURE OF THE INVENTION

The present invention is a method for producing an aryl ether produced by binding an aryloxy of hydroxyaryl with an organic group of organic halogen, which comprises reacting hydroxyaryl with organic halogen in gaseous carbon dioxide or supercritical carbon dioxide in the presence of base and onium salt. Desirably the present invention is the method for producing of said aryl ether which uses the onium salt by catalytic amount. More desirably, the onium salt is the compound represented by general formula of $R^1R^2R^3R^4N^+X^-$ or $R^1R^2R^3R^4P^+X^-$ (wherein $R^1$, $R^2$, $R^3$, $R^4$ respectively indicate a substituted or an un-substituted alkyl group, a cyclo-alkyl group, an alkenyl group, a cyclo-alkenyl group, an aryl group, an aralkyl group, an aralkenyl group, an alkenaryl group or an alkaryl group. $R^1$, $R^2$, $R^3$, $R^4$ can be same or can be different, and one to three of them can be a hydrogen atom. X indicates a halogen atom, a hydroxyl group, a hydrogensulfate group, a hydrogenphosphate group, a hydrogenphosphite group or a hydrophosphite group.). Further desirably, the present invention is the method for production of aryl ether wherein the base is a carbonate salt or a phosphoric salt of alkali metal or alkali earth metal (more than 2 can be used together with).

BRIEF ILLUSTRATION OF DRAWINGS

THE BEST EMBODIMENT TO CARRY OUT THE INVENTION

Figure 1:
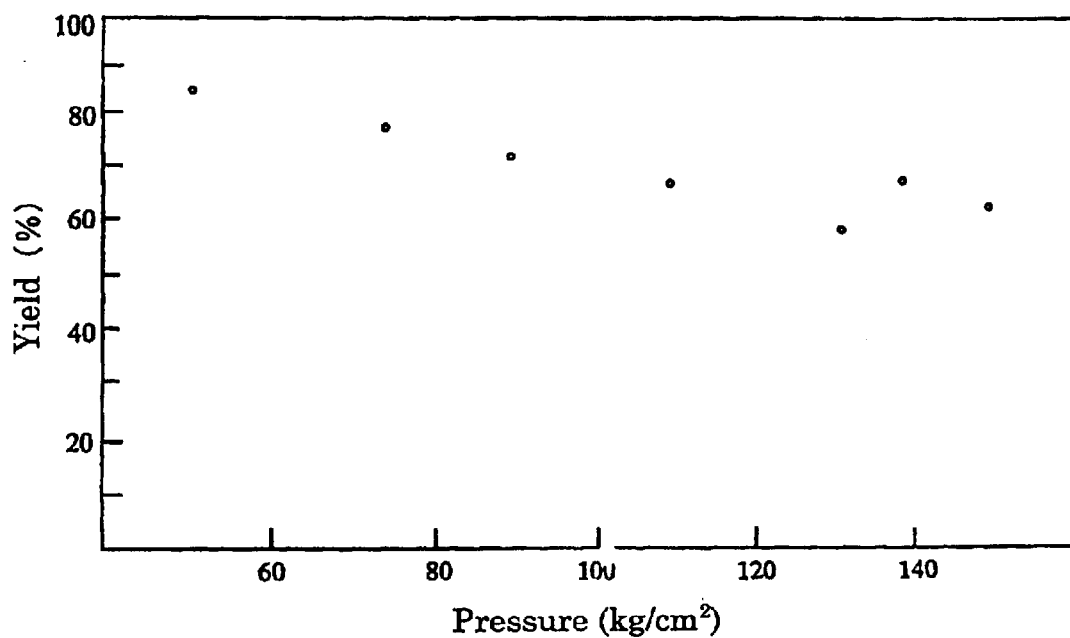
FIG. 1 is the drawing showing the relationship between pressure and yield.

The present invention will be illustrated more in detail according to the following description.

A. The gaseous state or supercritical state of carbon dioxide which composes the solvent for reaction is the condition used in the chemical reaction of the conventional technology. The condition of gaseous state carbon dioxide indicates the condition lower than 75.2 kg/cm$^2$ (7.4 MPa) in which carbon dioxide is gaseous state, and the supercritical state of carbon dioxide indicates the condition higher than critical temperature of 31.0° C. and critical pressure of 75.2 kg/cm$^2$ (7.4 MPa). In the reactive condition, the upper limit for temperature and pressure are not restricted, however, referring to the temperature, it is lower than the heat decomposing temperature of the compounds of starting materials and catalyst (the reaction progresses at relatively mild condition from 60° C. to 120° C.). Regarding to the pressure, the desirable range is from 10 to 140 kg/cm$^2$ (1 to 13.7 MPa), because the higher pressure for reaction raises the cost for apparatus. When the pressure for reaction is higher than 200 kg/cm$^2$ (19.6 MPa), the yield of product is deteriorated. Further, when the pressure is dropped to 1 atomic pressure (0.1 MPa), the yield of product is also deteriorated.

As the apparatus for reaction, a conventional reactor used for the reaction using supercritical state carbon dioxide such as a batch type reactor, a continuous vessel type reactor, a piston flow circulation type reactor or a tower circulation type reactor can be used.

B. As a base used in the present invention, a salt of alkali metal can be used. For instance, a carbonate, a hydrogencarbonate, a phosphate, a sulfate, a hydrogensulfate, a carboxylate or a sulfonate can be mentioned as a desirable example, and as the more desirable example, potassium carbonate can be mentioned. At the actual reaction, more than two kinds of above mentioned bases can be used together with.

C. As the onium salt, ammonium salt or phosphonium salt represented by general formula (1) $R^1R^2R^3R^4Q^+X^-$ can be mentioned. (in the formula, $R^1$, $R^2$, $R^3$ and $R^4$ respectively indicate a substituted or an unsubstituted alkyl group, a cycloalkyl group, an alkenyl group, a cycloalkenyl group, an aryl group, an aralkyl group, an aralkenyl group, an alkenaryl group or an alkaryl group. $R^1$, $R^2$, $R^3$, $R^4$ can be same or can be different, and one to three of them can be a hydrogen atom. X indicates a halogen atom, a hydroxyl group, a hydrogensulfate group, a hydrogenphosphate group, a hydrogenphosphite group or a hydrophosphite group. Q is N or P.) When $Bu_4$,Nl is used, the reaction can be progressed effectively. At the reaction, two kinds of above mentioned onium salt can be used together with.

D. As hydroxyaryl (phenols), various kinds of compound which has at least one hydroxyl group can be used and can be voluntarily selected in connection with the desired compound (use). For example, in a case of a material for liquid crystal, p-phenylphenols can be mentioned as the desirable example.

E. Same to the above, various kinds of compound can be used as an organic halogen, and can be voluntarily selected in connection with the desired compound.

EXAMPLES

General conditions for reaction 5 to 30 milli mole of base, 0.1 to 3 milli mole of onium salt, 2 to 10 milli mole of organic halogen compound and 5 milli mole of phenol compound are poured into a reacting vessel of 50 ml (for example, an autoclave made of stainless steel; which is for a batch type reactor, further, well-known apparatus for a continuous production can be used). Possible amount of phenol compound to be poured into a reacting vessel of 50 ml is 0.1 to 20 milli mole, and when the amount of phenol compound is changed, the amount of other reagents must be changed according to the changed ratio of the phenol compound. The inside atmosphere of the reacting vessel is replaced by carbon dioxide for two times, then liquid carbon dioxide is added at ordinary temperature and heated to the temperature in the region of 40 to 200° C. The inner pressure becomes to the prescribed pressure value. The desirable range of the inner pressure is from 10 to 250 kg/cm$^2$ (from 1 to 24.5 MPa). The mixture is heated at above mentioned temperature for 1 to 24 hours, the reacting vessel is cooled down by ice so as to recover the inner pressure to the normal pressure. Thus aryl ether can be obtained.

In the present invention, the reacting temperature of 100° C. around is used as the desirable reacting condition.

Example 1

Potassium carbonate (1.38 g, 0.01 mol), tetrabutylammonium bromide (0.081 g, 0.00025 mol), phenol (0.47 g, 0.005 mol) and benzyl chloride (1.00 g, 0.0079 mol) are poured into an autoclave made of stainless steel (pressure vessel) of 50 mL. The inside atmosphere of the autoclave is replaced by carbon dioxide for two times, then liquid carbon dioxide (13.7 g) is added at ordinary temperature. By heating at 100° C., the inner pressure becomes 90 kg/cm$^2$ (8.8 MPa). The mixture is stirred for one hour at 100° C., the reacting vessel is cooled down using ice and the inner pressure is recovered to the normal pressure, then extracted with chloroform (2×20 mL). The extracted product is washed with diluted hydrochloric acid then rinsed with water, and dried over anhydrous sodium sulfate. 50 mL is measured using a measuring flask, and 5 mL is picked up from which and the obtained amount is calculated by $^1$HNMR using coumarin as an internal standard substance (73%).

Above mentioned reaction can be indicated by following reacting formula.

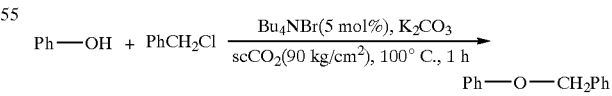

Example 2

This Example indicates the case when organic halogen compound and phenol are changed.

Potassium carbonate (1.38 g, 0.01 mol), tetrabutylammonium bromide (0.081 g, 0.00025 mol), phenols (0.005 mol) and organic halogen compound (0.0075 mol) are poured into an autoclave made of stainless steel (pressure vessel) of 50 mL. The inside atmosphere of the autoclave is replaced by carbon dioxide for two times, then liquid carbon dioxide (13.7 g) is added at the ordinary temperature. By heating at 100° C., the inner pressure becomes 90 kg/cm² (8.8 MPa). The mixture is stirred for one hour at 100° C., the reacting vessel is cooled down using ice and the inner pressure is recovered to the normal pressure, then extracted with chloroform (2×20 mL). The extracted product is washed with diluted hydrochloric acid then rinsed with water, and dried over anhydrous sodium sulfate. 50 mL is measured using a measuring flask, and 5 mL is picked up from which and the obtained amount is calculated by $^1$HNMR using coumarin as an internal standard substance. The residue solution is concentrated and distilled with a Kugel roll, or solid product is recrystallized so as to obtain arylether. After converted, yield for isolation can be obtained.

The effect of organic halogen compound is shown in Table 1 and the effect of para-substituted phenol is shown in Table 2.

TABLE 1

Effect of organic halogen compound

Ph—OH + RX $\xrightarrow[\text{scCO}_2(90 \text{ kg/cm}^2),]{\text{Bu}_4\text{NBr, K}_2\text{CO}_3}$ Ph—O—R
(5 mmol)   (7.7 mmol)   100° C., 1 h

| RX | K$_2$CO$_3$, mmol | Bu$_4$NBr, mmol | Yield, % |
|---|---|---|---|
| PhCH$_2$Cl | 10 | 5 | 73 |
| PhCH$_2$Cl | 20 | 5 | 96 |
| PhCH$_2$Br | 10 | 5 | 96 |
| CH$_2$=CHCH$_2$Br | 10 | 5 | 56 |
| CH$_3$(CH$_2$)$_5$I | 10 | 5 | 56 |
| CH$_3$(CH$_2$)$_7$Br | 10 | 5 | 38 |
| CH$_3$(CH$_2$)$_7$Br | 10 | 10 | 77 |

TABLE 2

Effect of para-substituted phenol

R-phenylene-OH + CH$_3$(CH$_2$)$_7$Br $\xrightarrow[\text{scCO}_2(90 \text{ kg/cm}^2),]{\text{Bu}_4\text{NBr(20 mol \%)}, \text{K}_2\text{CO}_3(20 \text{ mml})}$
(5 mmol)   (7.5 mmol)   100° C.

R-phenylene-OCH$_3$(CH$_2$)$_7$CH$_3$

| R | Time, h | Yield, % |
|---|---|---|
| H | 2 | quantitative |
| CH$_3$ | 2 | quantitative |
| CH$_3$O | 2 | 86 |
| Ph | 3 | quantitative(94) |
| CH$_3$CO | 3 | quantitative(93) |
| PhOCO | 3 | quantitative(94) |
| CN | 3 | 97 | numerical value in parenthesis is yield for isolation

Example 3

This Example indicates the case when a compound used for catalyst and base compound are changed.

Base (0.01 mol), catalyst (0.00025 mol), phenol (0.47 g, 0.005 mol) and benzyl chloride (0.96 g, 0.0075 mol) are poured into an autoclave made of stainless steel pressure vessel) of 50 mL. The inside atmosphere of the autoclave is replaced by carbon dioxide for two times, then liquid carbon dioxide (13.7 g) is added at ordinary temperature. By heating at 100° C., the inner pressure becomes 90 kg/cm² (8.8 MPa). The mixture is stirred for one hour at 100° C., the reacting vessel is cooled down using ice and the inner pressure is recovered to the normal pressure, then extracted with chloroform (2×20 mL). The extracted product is washed with diluted hydrochloric acid then rinsed with water, and dried over anhydrous sodium sulfate. 50 mL is measured using a measuring flask, and 5 mL is picked up from which and the obtained amount is calculated by $^1$HNMR using coumarin as an internal standard substance.

The effect of catalyst is shown in Table 3 and the effect of base is shown in Table 4.

TABLE 3

Effect of catalyst

Ph—OH + PhCH$_2$Cl $\xrightarrow[\text{scCO}_2(90 \text{ kg/cm}^2),]{\text{catalyst(5 mol \%)}, \text{K}_2\text{CO}_3(10 \text{ mml})}$ Ph—O—CH$_2$Ph
(4 mmol)   (7.5 mmol)   100° C., 1 h

| onium salt(catalyst) | Yield, % |
|---|---|
| Bu$_4$NCl | 65 |
| Bu$_4$NBr | 73 |
| Bu$_4$NI | quantitative |
| Bu$_4$PBr | 75 |
| Me$_3$BnNCl | 53 |
| [CH$_3$(CH$_2$)$_{15}$NMe$_2$Et]Br | 61 |
| [CH$_3$(CH$_2$)$_7$]$_3$MeNCl | 73 |

TABLE 4

Base compound is changed

Ph—OH + PhCH$_2$Cl $\xrightarrow[\text{scCO}_2(90 \text{ kg/cm}^2),]{\text{Bu}_4\text{NBr(5 mol \%)}, \text{base(10 mml)}}$ Ph—O—CH$_2$Ph
(4 mmol)   (7.5 mmol)   100° C., 1 h

| base | Yield, % |
|---|---|
| Na$_2$CO$_3$ | 29 |
| K$_2$CO$_3$ | 73 |
| Cs$_2$CO$_3$ | 68 |
| K$_3$PO$_4$ | 68 |

Example 4

At the temperature condition of 100° C., the relationship between pressure and yield is investigated.

The obtained results are shown in FIG. 1.

Figure 2:
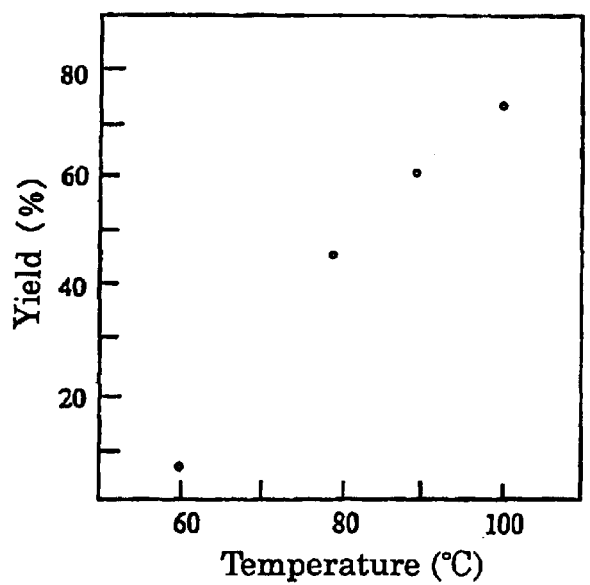
FIG. 2 is the drawing showing the relationship between temperature and yield.

The pressure is settled to the constant value of 90 kg/cm² (8.8 MPa), and the relationship between temperature and yield is investigated The obtained results are shown in FIG. 2.

Example 5

Potassium carbonate (1.38 g, 0.01 mol), tetrabutylammonium bromide (0.163 g, 0.00051 mol), anthrone (is in taotomeric isomer relation with 9-hydroxyanthracene. During a reaction, it forms a hydroxy type) (0.927 g, 0.005 mol) and butyl bromide (1.04 g, 0.0076 mol) are poured into an autoclave made of stainless steel (pressure vessel) of 50 mL. The inside atmosphere of the autoclave is replaced by carbon dioxide for two times, then liquid carbon dioxide (14.4 g) is added at the ordinary temperature. By heating at 100° C., the inner pressure becomes 98 kg/cm² (9.6 MPa). The mixture is stirred for one hour at 100° C., the reacting vessel is cooled down using ice and the inner pressure is recovered to the normal pressure, then extracted with chloroform (2×20 mL). 50 mL is measured using a measuring flask, and 5 mL is picked up from which and the yield of 9-buthoxyanthracene is calculated by ¹HNMR using coumarin as an internal standard substance. The obtained yield is 84%.

POSSIBILITY FOR THE INDUSTRIAL USE

As mentioned above, an excellent effect that the useful chemical compounds can be obtained in the condition being gentle to the environment can be provided by the present invention.

What is claimed is:

1. A method for producing an aryl ether produced by bonding an aryloxy of hydroxyaryl with an organic group of organic halogen, which comprises reacting hydroxyaryl with organic halogen using gaseous carbon dioxide or supercritical carbon dioxide as a reaction medium in the presence of base and onium salt.

2. The method for producing the aryl ether of claim 1, wherein the amount of onium salt is the catalytic amount.

3. The method for producing the aryl ether in accordance with claim 1, wherein the onium salt is the compound represented by general formula of $R^1R^2R^3R^4N^+X^-$ or $R^1R^2R^3R^4N^-$, wherein $R^1$, $R^2$, $R^3$, $R^4$ respectively indicate a substituted or an unsubstituted alkyl group, a cycloalkyl group, an alkenyl group, a cycloalkenyl group, an aryl group, an aralkyl group, an aralkenyl group, an alkenaryl group or an alkaryl group, $R^1$, $R^2$, $R^3$, $R^4$ can be same or can be different, and one to three of them can be a hydrogen atom, and X indicates a halogen atom, a hydroxyl group, a hydrogensulfate group, a hydrogenphosphate group, a hydrogenphosphite group or a hydrophosphite group.

4. The method for producing the aryl ether in accordance with claim 1, wherein the base is a carbonate salt or a phosphoric salt of alkali metal or alkali earth metal.

5. The method for producing the aryl ether in accordance with claim 2, wherein the onium salt is the compound represented by general formula $R^1R^2R^3R^4N^+X^-$ or $R^1R^2R^3R^4P^+X^-$, wherein $R^1$, $R^2$, $R^3$, $R^4$ respectively indicate a substituted or an unsubstituted alkyl group, a cycloalkyl group, an alkenyl group, a cycloalkenyl group, an aryl group, an aralkyl group, an aralkenyl group, an alkenaryl group or an alkaryl group, $R^1$, $R^2$, $R^3$, $R^4$ can be the same or can be different, and one to three of them can be a hydrogen atom, and X indicates a halogen atom, a hydroxyl group, a hydrogensulfate group, a hydrogenphosphate group, a hydrogenphosphite group or a hydrophosphites group.

6. The method for producing the aryl ether in accordance with claim 2 wherein the base is a carbonate salt or a-phosphoric salt of alkali metal or alkali earth metal.

7. The method for producing the aryl ether in accordance with claim 3 wherein the base is a carbonate salt or a phosphoric salt of alkali metal or alkali earth metal.

8. The method for producing the aryl ether in accordance with claim 5 wherein the base is a carbonate salt or a phosphoric salt of alkali metal or alkali earth metal.

* * * * *